US006322554B1

(12) United States Patent
Tomita

(10) Patent No.: US 6,322,554 B1
(45) Date of Patent: Nov. 27, 2001

(54) LASER TREATMENT APPARATUS

(75) Inventor: Seiki Tomita, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/431,101

(22) Filed: Nov. 1, 1999

(30) Foreign Application Priority Data

Nov. 2, 1998 (JP) .................................................. 10-311540

(51) Int. Cl.$^7$ .................................................. A61F 9/008
(52) U.S. Cl. .................................. 606/4; 606/10; 606/13
(58) Field of Search .............................. 606/4–6, 10–13

(56) References Cited

U.S. PATENT DOCUMENTS

| | | | |
|---|---|---|---|
| 4,409,979 | * 10/1983 | Roussel et al. | 606/4 |
| 4,499,897 | 2/1985 | Roussel . | |
| 4,561,436 | * 12/1985 | Nunnerlyn | 606/10 |
| 4,565,197 | * 1/1986 | Dahy | 606/4 |
| 5,013,311 | * 5/1991 | Nouri | 606/4 |
| 5,057,102 | * 10/1991 | Tomwka et al. | 606/4 |

FOREIGN PATENT DOCUMENTS 61-9063   3/1986   (JP) .

* cited by examiner

Primary Examiner—David M. Shay
(74) Attorney, Agent, or Firm—Finnegan, Henderson, Farabow, Garrett & Dunner, L.L.P.

(57) ABSTRACT

A laser treatment apparatus for irradiating an affected area of a patient with a treatment laser beam is disclosed. In the apparatus, the treatment laser beam is emitted by a laser source and delivered to the affected area through a treatment laser beam irradiation optical system to irradiate the affected area. An aiming light delivery optical system forms plural aiming light beams so that an optical axis of the treatment laser beam irradiation optical system is put between the aiming light beams, and delivers the plural aiming light beams to the affected area so that the aiming light beams are focused on a position on which the treatment laser beam is to be focused. During this focusing, the aiming beams are being rotated manually or automatically by a manual rotation mechanism or an automatic rotation mechanism. The rotating mode of the aiming beams is selected with a selection switch from a manual rotation mode and an automatic rotation mode.

12 Claims, 6 Drawing Sheets

LASER TREATMENT APPARATUS

BACKGROUND OF THE INVENTION

1. Field of the Invention

The present invention relates to a laser treatment apparatus for treating an affected area of a patient by irradiating the affected area with a treatment laser beam emitted from a laser source.

2. Description of Related Art

As one of laser treatment apparatus in the ophthalmic field, a YAG laser apparatus has been known. This YAG laser apparatus is used for incising the posterior capsule of a patient's eye to treat after cataract, ripping (or cutting) the vitreous fibers of a patient's eye to treat traction retinal detachment, and so on.

In general, when an operator operates a laser apparatus to irradiate an affected area of a patient to be treated with a treatment laser beam, the operator adjusts the focus of the laser apparatus on the affected area while observing a visible aiming light made coaxial with the treatment laser beam. As an aiming manner of the YAG laser apparatus, there is known a manner of separating (or dividing) aiming light into two luminous flux which will pass on opposite sides of an optical axis of a treatment laser beam, and then overlapping the two luminous flux one another at an aiming point on an affected area (so as to focus on the same position) thereby to facilitate the aiming in a focusing direction. In such the apparatus using the above aiming manner, one fixedly divides the aiming light into two luminous flux in a vertical (i.e., longitudinal) direction or a horizontal (i.e., lateral) direction with respect to an eye to be treated, and another is provided with a rotary function of automatically rotating the aiming light in order to check the overlapping state of the two aiming light beams overlapped one another at one point.

Meanwhile, in the case of posterior capsule incision, the posterior capsule is clouded, which easily reflects the aiming light, so that each position of the two divided aiming light beams can be clearly observed. Accordingly, overlapping the divided aiming light beams at a point is not much difficult. At this time, it is very convenient to automatically rotate the aiming light beams for the purpose of confirming the overlapping state of the aiming light beams.

However, when cutting of the vitreous fibers for traction retinal detachment treatment is carried out, normal portions of the vitreous fibers being transparent, the positions of the aiming light beams are very hard to observe unless the aiming light beams properly fall on the clouded vitreous fibers that pull the retina. Accordingly, in the case where the divisional direction of the aiming light beams differs from the extending direction of the vitreous fibers in the area to be cut, both of the two aiming light beams can not be observed at the same time. When only one of the aiming light beams is observable, it is difficult to determine whether the aiming light beams are overlapped one another (which means that the aiming light beams come into focus at the same point) or only one of the two aiming light beams is viewed. Therefore, it takes a much time to confirm aiming propriety and perform proper aiming (alignment). Alternatively, when the vitreous fibers are cut with the apparatus having the automatic rotating function of aiming light, similarly, fine adjustment is hard and the positions of the aiming light beams can not be confirmed. This may require a long time for conducting proper aiming (alignment) of the apparatus to the affected area of a patient.

SUMMARY OF THE INVENTION

The present invention has been made in view of the above circumstances and has an object to overcome the above problems and to provide a laser treatment apparatus which enables an operator to easily confirm an aiming (or alignment) state of the apparatus with respect to a treatment area of a patient even if it has directivity, and to efficiently conduct treatment on the treatment area.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for irradiating an affected area of a patient with a treatment laser beam, the apparatus including a laser source which emits the treatment laser beam, an irradiation optical system for delivering the treatment laser beam emitted from the laser source to the affected area to irradiate it, an aiming light delivery optical system for forming plural aiming light beams so that an optical axis of the treatment laser beam irradiation optical system is put between the aiming light beams, and delivering the plural aiming light beams to the affected area so that the aiming light beams are focused on a position on which the treatment laser beam is to be focused, manual rotation means for manually rotating the aiming light beams about the irradiation optical axis, automatic rotation means for automatically rotating the aiming light beams about the irradiation optical axis, and selection means for selecting a mode to rotate the aiming light beams from a manual rotation mode conducted by the manual rotation means and an automatic rotation mode conducted by the automatic rotation means.

According to another aspect of the present invention, there is provided a laser treatment apparatus for irradiating an affected area of a patient with a treatment laser beam, the apparatus including a laser source which emits the treatment laser beam, an irradiation optical system for delivering the treatment laser beam emitted from the laser source to the affected area to irradiate it, an aiming light delivery optical system including an aiming light source which emits aiming light used for focusing the treatment laser beam to the affected area and a beam dividing member for dividing the aiming light into plural light beams so that an optical axis of the treatment laser beam irradiation optical system is put between the divided aiming light beams, and for delivering the plural aiming light beams to the affected area so that the aiming light beams are focused on a position on which the treatment laser beam is to be focused, a rotating unit including a rotating member which holds the beam dividing member and is rotatable about the irradiation optical axis, a knob and a first gear mechanism for manually rotating the rotating member, a motor and a second gear mechanism for electrically rotating the rotating member, a control unit for driving the motor, and a switch for generating a driving signal to the control unit.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
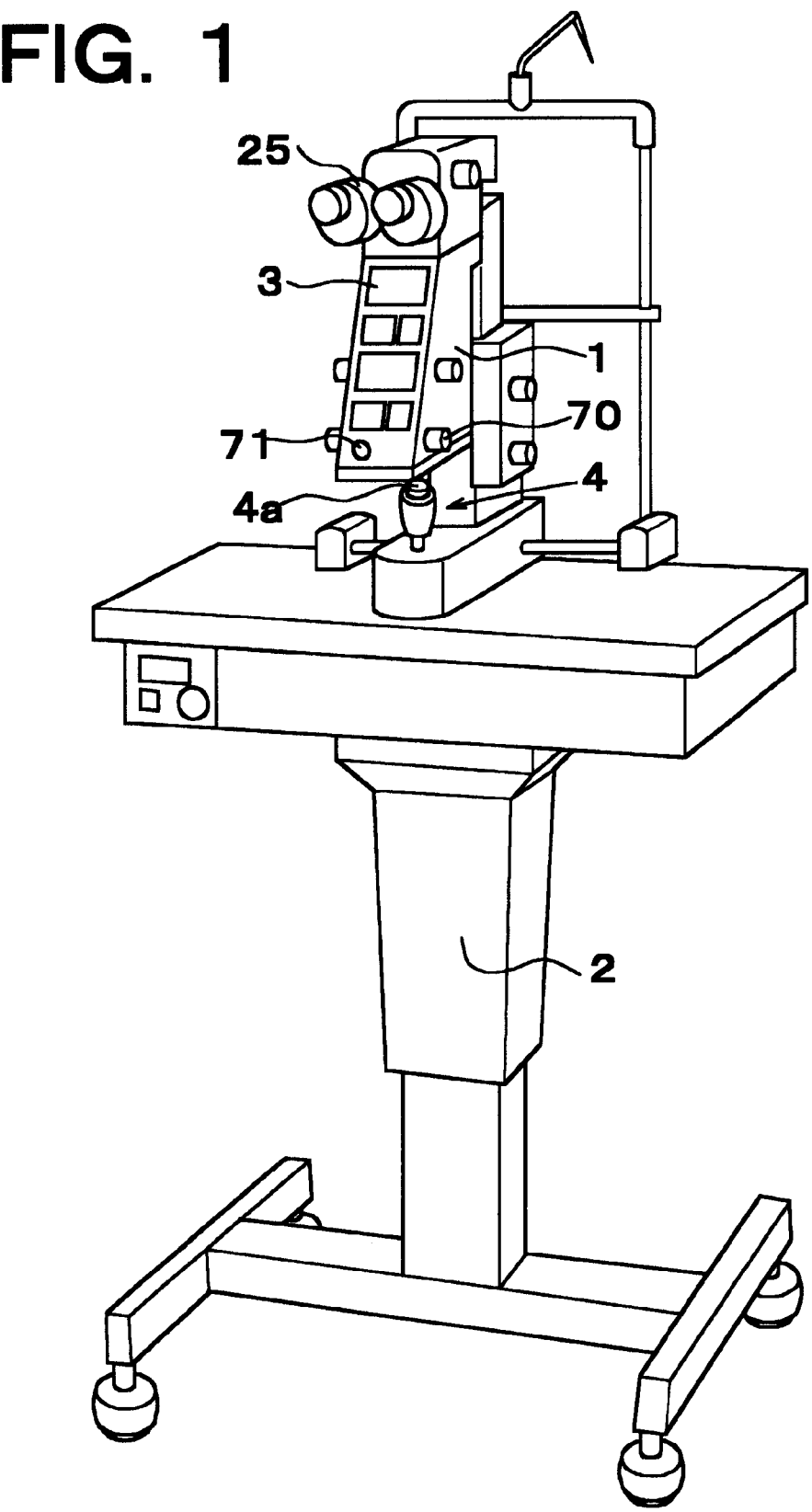
FIG. 1 is a perspective view of a preferred embodiment of a laser treatment apparatus according to the present invention.

A detailed description of one preferred embodiment of a laser treatment apparatus embodying the present invention will now be given referring to the accompanying drawings. FIG. 1 is a perspective view of the laser treatment apparatus in the present embodiment.

Numeral 1 denotes a main body of the laser treatment apparatus, which is provided therein with a treatment laser source, an aiming light source, a light delivery optical system, and others. This main body 1 is mounted on a base stand 2 which is movable in a vertical direction. Numeral 4 denotes a joystick for moving the main body 1 on a table of the stand 2 in a back-to-front and a right-to-left directions, thereby achieving the proper alignment of the main body 1 with respect to an affected area of a patient's eye prior to an irradiating operation thereon with a treatment laser beam. The alignment in a vertical direction is conducted by operating a rotary knob of the joystick 4 to vertically move the main body 1. The joystick 4 is also provided with a trigger switch 4a disposed on its top part. The trigger switch 4a is pushed to start the emission of a treatment laser beam. Numeral 3 denotes a control panel for setting various laser irradiation conditions. Numeral 70 denotes a knob for causing the rotation of aiming light, which will be mentioned later in detail.

Figure 2:
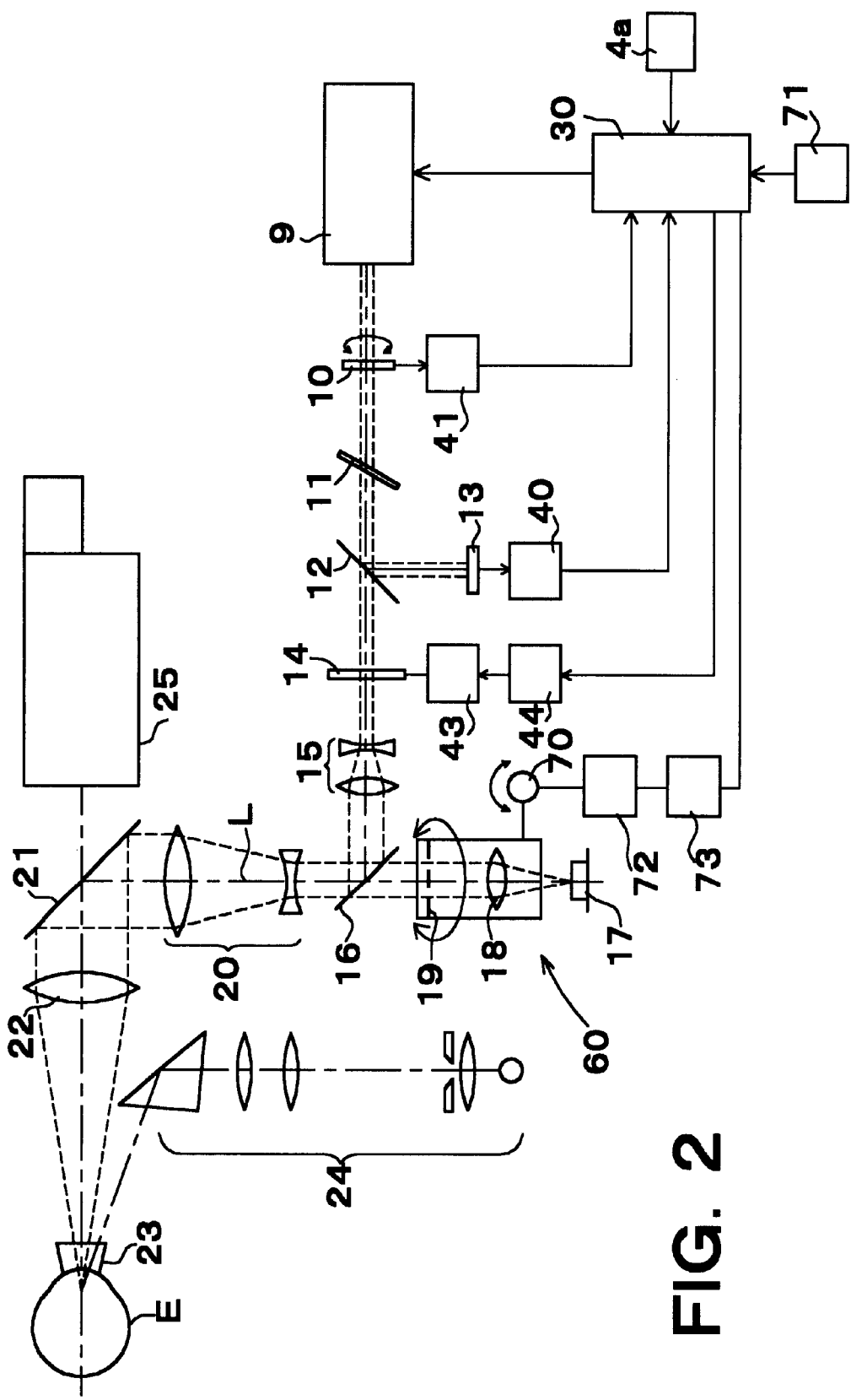
FIG. 2 is a block diagram of an optical system and a control system in the laser treatment apparatus in the embodiment.

FIG. 2 is a block diagram of an optical system and a control system of the laser apparatus in the present embodiment. As shown in FIG. 2, the optical system and the control system are configured by the following elements.

Numeral 9 is a YAG laser source which emits a treatment laser beam (hereinafter, simply referred to as a treatment beam) having a main wavelength of 1064 nm; 10, a ½ wave plate for rotating the polarizing direction of the treatment beam; 11, a polarizing plate disposed at a Brewster angle; 12, a beam splitter; and 13, a photosensor.

The wave plate 10 is rotated by the operation of an energy adjustment knob not shown. This wave plate 10 serves, in cooperation with the polarizing plate 11, to adjust the energy level of the treatment beam to irradiate the affected area. A part of the treatment beam passed through the polarizing plate 11 is reflected by the beam splitter 12 and detected by the photosensor 13.

Numeral 14 is a safety shutter which is inserted in the optical axis of the treatment beam to block it in predetermined cases, for example, when test irradiation is conducted or when abnormal conditions are encountered. In a normal condition, where the shutter 14 is out of the optical axis, the treatment beam emitted from the YAG laser source 9, passed through the wave plate 10, the polarizing plate 11, and the beam splitter 12 is expanded by expander lenses 15. The thus expanded treatment beam is deflected by a dichroic mirror 16 toward expander lenses 20 so that the deflected treatment beam becomes coaxial with an aiming beam mentioned later.

Numeral 17 is a laser diode which emits an aiming light beam having a wavelength (a main wavelength is 633 nm) in a visible range. The aiming light beam emitted from the laser diode 17 is passed through a lens 18 and made into parallel flux, and passed through an aperture plate 19 having two apertures disposed symmetrically with respect to the optical axis L to divide a light beam into two luminous flux. The aperture plate 19 is attached to a rotation mechanism unit 60 and allowed to rotate about the optical axis L in response to the manual operation of the knob 70. The structure of the rotation mechanism unit 60 will be described later in detail.

Numeral 20 are expander lenses for expanding the treatment beam and the aiming beams. Numeral 21 is a dichroic mirror which reflects the treatment beam and a part of the aiming beams, while transmits an observation light (configured by an aiming light and a slit light mentioned later reflected by the patient's eye). This dichroic mirror 21 makes the optical axis L coaxial with the optical axis of an objective lens 22. The treatment beam reflected by the dichroic mirror 21 is focused on an affected area of a patient's eye E through the objective lens 22 and a contact lens 23 placed on the eye E. The two divided aiming beams are reflected by the dichroic mirror 21 and focused at a focusing position, which is a reference point for irradiation of the treatment beam, through the objective lens 22 and the contact lens 23. It is to be noted that the focusing position of the treatment beam can also be shifted with respect to the focusing position of the aiming beams by moving the expander lenses 15 in the optical axis.

Numeral 24 is an optical system for projecting slit light. The luminous flux from this optical system 24 is delivered to the patient's eye E through the contact lens 23 to illuminate the eye E. Numeral 25 is a binocular microscope through which an operator observes the patient's eye E illuminated by the slit light projected from the slit light projecting optical system 24.

Numeral 30 is a control unit for controlling the whole apparatus. Numeral 40 is a detection circuit for processing a detection signal transmitted from the photosensor 13. The processed signal in the detection circuit 40 is transmitted to the control unit 30. Numeral 41 is a potentiometer for detecting a rotational position of the wave plate 10. The adjustment of the energy level of the treatment beam to be delivered to the eye E is determined according to the rotational position of the wave plate 10. Accordingly, upon reception of a detection signal from the potentiometer 41 that detects the rotational position of the wave plate 10, the control unit 30 causes a display panel not shown to display the intended energy level in correspondence to the detection signal, so that the operator can confirm the intended energy level of the treatment beam to irradiate the treatment area of the eye E.

Numeral 43 is a motor connected to the shutter 14 for driving the shutter 14 to open or close. Numeral 44 is a driving circuit which is controlled in response to a control signal from the control unit 30 for driving the motor 43.

Numeral 72 is a motor for causing an automatic rotation of the rotation mechanism unit 60. Numeral 73 is a driving circuit for driving the motor 72. The control panel 3 is also provided with a mode selection switch 71 for selectively switching the rotation mode of the rotation mechanism unit 60, i.e., of the aiming beams, from a manual rotation (a manual mode) by an operator to an automatic rotation (an automatic mode) by the motor 72, and vice versa. When the automatic mode is selected with the switch 71, the control unit 30 causes the driving circuit 73 to drive the motor 72 to thereby rotate the rotation mechanism unit 60.

Figure 3:
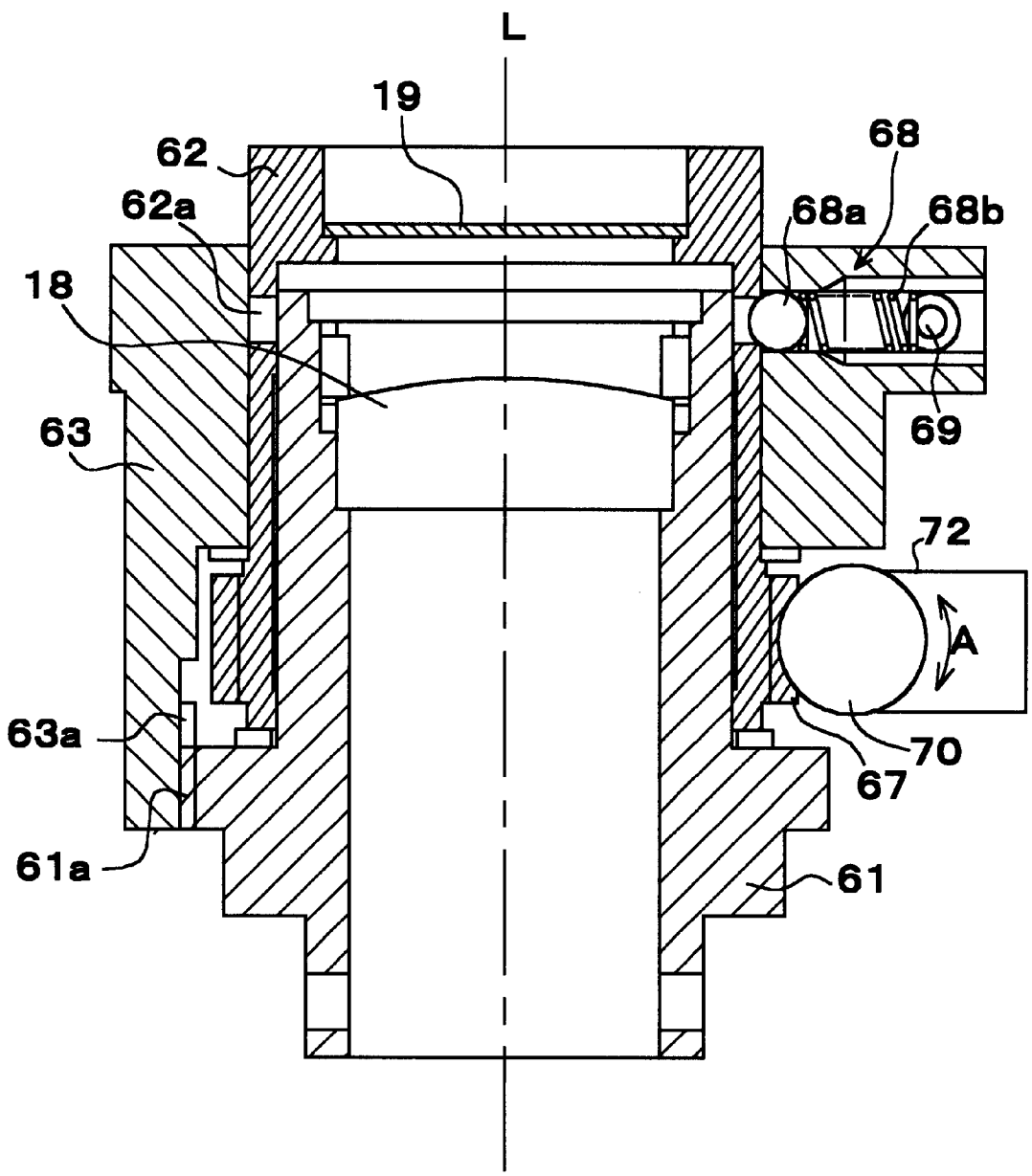
FIG. 3 is a schematic sectional view of a rotation mechanism of the laser treatment apparatus in the embodiment.

FIG. 3 is a schematic sectional view of the rotation mechanism unit 60. This rotation mechanism unit 60 is constructed of the following elements.

Numeral 61 is an inner cylindrical member which holds the lens 18 therein. A males crew 61a is formed on the outer periphery of a horizontal extending portion of the inner cylindrical member 61. Numeral 63 is anoutercylindrical member with a female screw 63a formed on its lower inside surface. The inner and outer cylindrical members 61 and 63 are screwed to each other through the male and female screws 61a and 63a and are fastened in the apparatus with screws. A part of the lower portion of the outer cylindrical member 63 is cut off so as not to obstruct the attachment and the rotation of the knob 70 which will be mentioned later.

Numeral 62 is a rotating member in which the aperture plate 19 is fixedly attached. This rotating member 62 is rotatably disposed between the inner and outer cylindrical members 61 and 63. At a lower part of the rotating member 62, a spiral screw gear 67 is formed. This screw gear 67 engages with a spiral gear 74 fixed to a shaft 76 of the knob 70 (see FIG. 6). With the engagement between those spiral gears, the rotation of the knob 70 in a direction indicated by an arrow A is transmitted to the rotating member 62 through the gears 74 and 67, thereby causing the rotation of the aperture plate 19 placed on the rotating member 62 about the optical axis L. A gear ratio between the gear 67 and a gear 74 of the knob 70 is designed such that one turn of the knob 70 causes a quarter turn of the aperture plate 19 (the rotating member 62). Since the rotational amount (i.e., a rotational angle) of the aperture plate 19 is small compared with the rotational amount (i.e., a rotational angle) of the knob 70 which is rotated by the operator, finer adjustment of the rotational angle of the aiming beams which are formed through the aperture plate 19 can be conducted.

The rotation mechanism unit 60 is also provided with a click mechanism 68 disposed in an upper portion of the outer cylindrical member 63. The click mechanism 68 includes a ball 68a and a spring 68b. This spring 68b has one end in contact with the ball 68a and another end fixed by a stopper 69 provided in the outer cylindrical member 63, so that the spring 68b always urges the ball 68a to the rotating member 62. In the rotating member 62 are formed concave portions 62a for receiving the ball 68a of the click mechanism 68, at equal intervals of 90-degrees. The relation between the click mechanism 68 and the aperture plate 19 is designed so that the operator who observes the patient's eye E through the microscope 25 while rotating the knob 70 feels a click when the aiming beams which have been divided through the aperture plate 19 are aligned in a vertical direction or a horizontal direction within a microscopic visual field. Since the rotating member 62 is rotated a quarter turn (90 degrees) for one turn of the knob 70, the operator has a click feeling through the knob 70 every one turn of the knob 70. Thus, the click mechanism 68 serves to allow the operator to recognize the rotating state of the aiming light beams divided by the aperture plate 19 and rotated with the rotation of the rotating member 62 caused by the manual operation of the knob 70.

Figure 6:
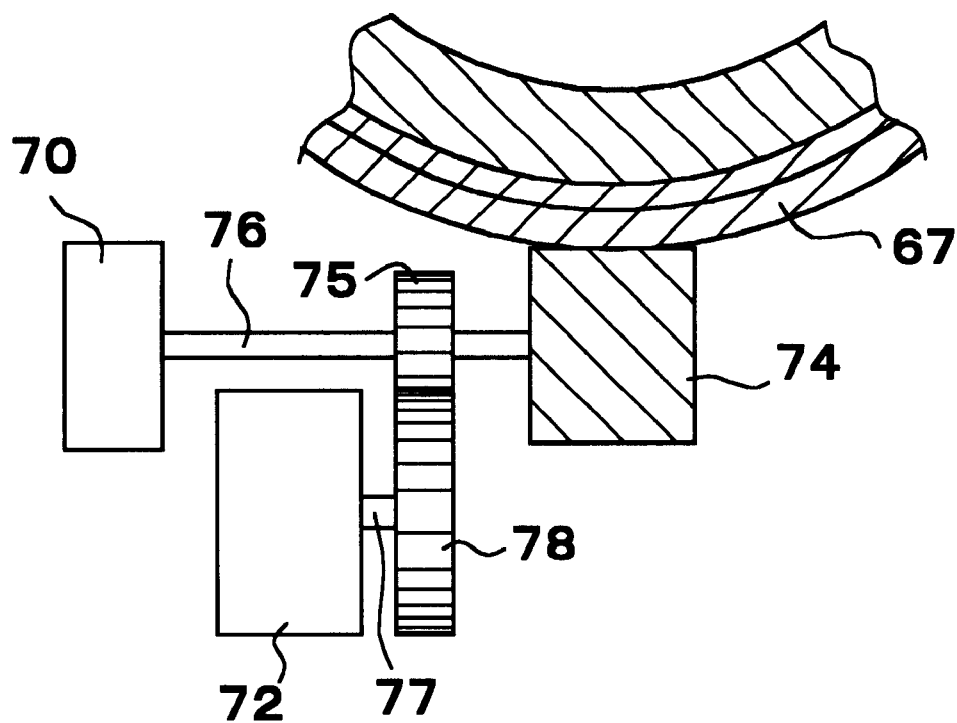
FIG. 6 is a schematic plan view of gear mechanisms used in the rotation mechanism shown in FIG. 3.

The motor 72 is connected to a gear 75 fixed to the shaft 76 of the knob 70 through a rotating gear 78 fixed to a shaft 77 of the motor 72, as shown in FIG. 6. Driving the motor 72 can cause the rotation of the gear 67 of the rotating member 62 through the gear 74 of the knob 70 which engages with the gear 67.

Next, the operation of the laser treatment apparatus configured as above will be described below.

First, a case where the apparatus is used for posterior capsule incision is explained. An operator sets irradiation conditions on the control panel 3, and operates the switch 71 to select an automatic mode as the rotation mode of aiming light. The operator then operates the joystick 4 to move the main body 1 with respect to a patient's eye E to be treated while observing the eye E through the microscope 25 such that the two divided aiming beams are focused on the affected area intended to be incised, and overlapped one another at one point. When the apparatus is out of alignment in a focusing direction with respect to the affected area of the eye E, the aiming beams are not completely overlapped one another and such the partially overlapped aiming beams are seen in a flat shape. During the operation, the aiming beams are being rotated. The two aiming beams when they are so completely overlapped as seen to be one do not change positions even if rotated. On the other hand, the two aiming beams when overlapped with slight displacement change positions by the rotation, which is easy for the operator to observe. To bring the apparatus into proper alignment, the operator conducts fine adjustment of the apparatus with the joystick 4. Accordingly, the alignment of the apparatus with respect to the patient's eye E can be precisely achieved. Upon completion of the alignment using the aiming beams, the operator pushes the trigger switch 4a to start irradiation of a pulse of treatment light, thereby treating the affected area of the eye E.

Next, explanation is made on another case where the apparatus is used for ripping or cutting the vitreous fibers of a patient's eye to treat traction retinal detachment thereof.

An operator first selects a manual mode with the switch 71 to manually rotate the aiming beams. He conducts alignment of the apparatus in the same manner as mentioned above, while observing the inside of the patient's eye E through the microscope 25, such that the aiming beams are overlapped one another on a cutting point of the vitreous fibers.

Figure 4:
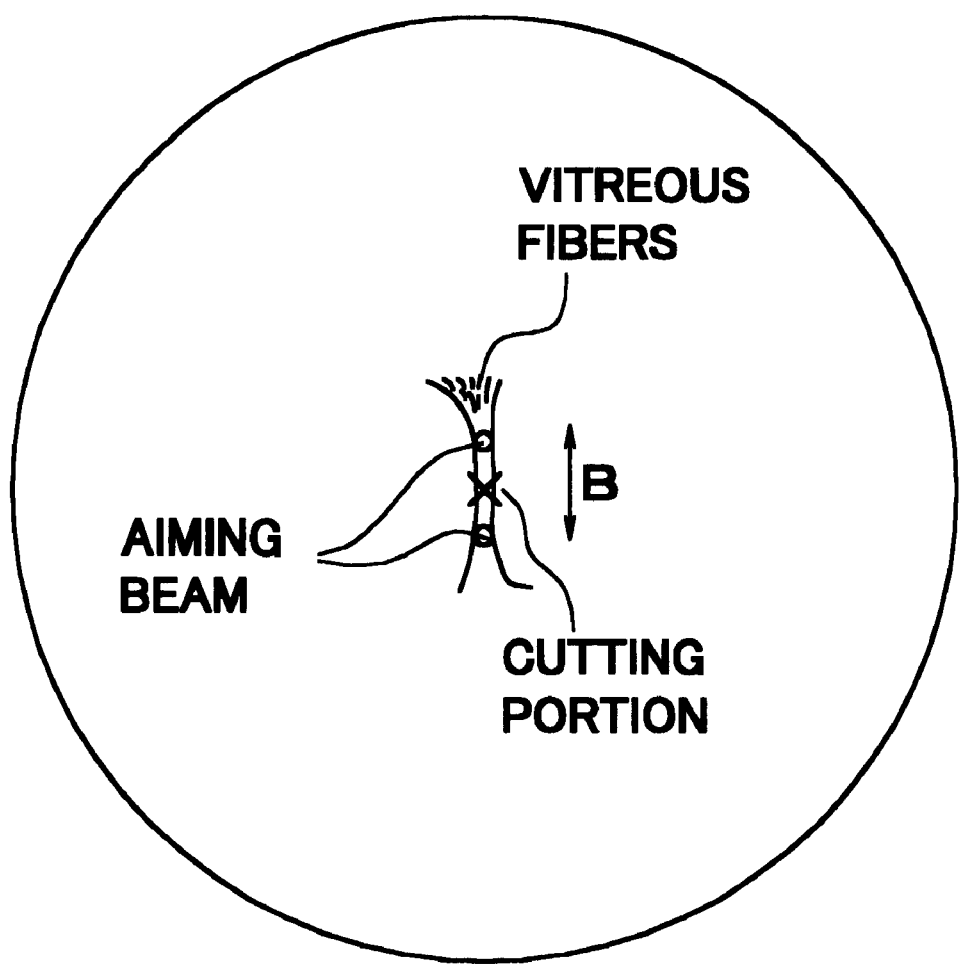
FIG. 4 is a schematic view of an example of the state of vitreous fibers that pull a retina of a patient's eye and an aiming light beams.
Figure 5A:
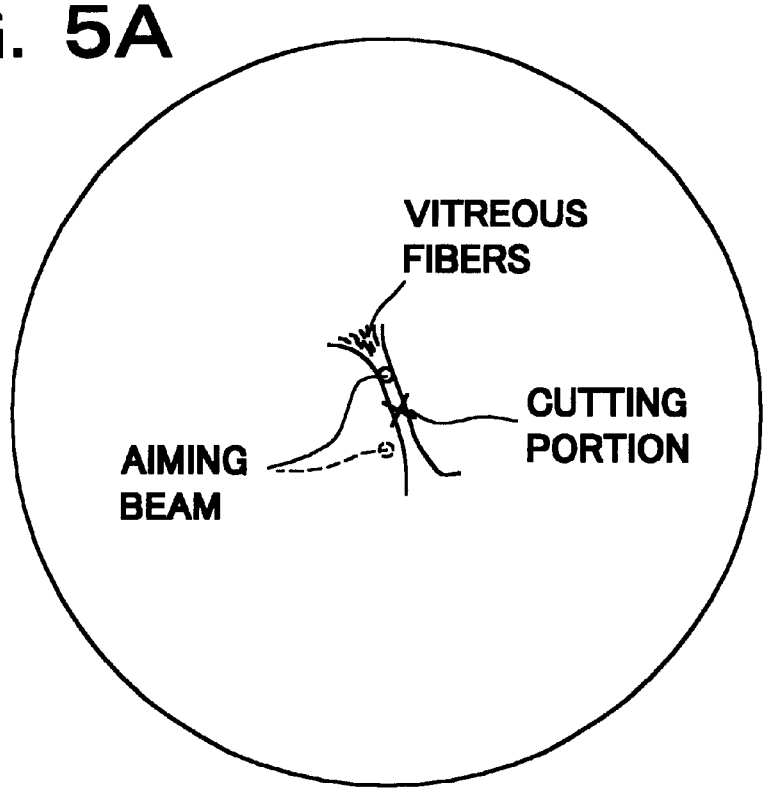
FIGS. 5A and 5B are schematic views of different examples of the states of vitreous fibers that pull a retina of a patient's eye and an aiming light beams.
Figure 5B:
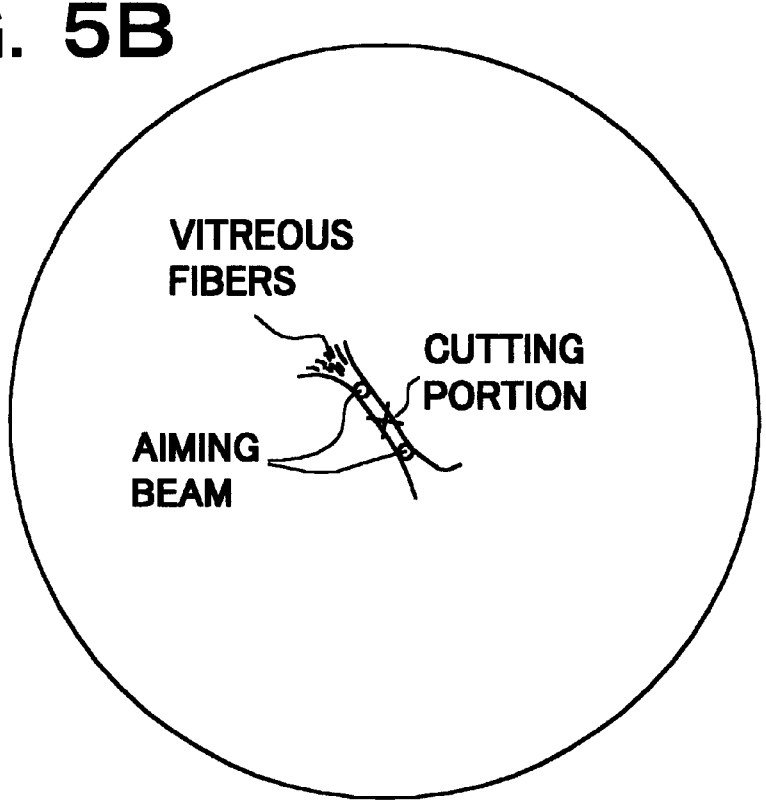

FIGS. 4, 5A and 5B are schematic views of the inside of the patient's eye E observed through the microscope 25, which show respective states of the vitreous fibers pulling the retina of the eye E and the aiming beams falling thereon. When an arrangement direction of the aiming beams which have been divided by the rotating member 62 (the aperture plate 19) rotated to a preset rotational angle and have been projected onto the treatment area of the eye E (namely, a rotational angle of the aiming beams rotated about the optical axis L) is almost the same as the extending direction (a direction B) of the vitreous fibers, the operator operates the joystick 4 to vertically and horizontally move the main body 1 so that the portion intended to be cut is viewed, as shown in FIG. 4, in the center of a microscopic visual field through the microscope 25 and in focus. As a result, both of the two divided aiming beams can be observed due to reflection by the vitreous fibers. When the operator can view the two aiming beams, he furthermore operates the joystick 4 and others until the aiming beams are overlapped one another at the cutting portion of the eye E to bring the apparatus in focus on the incising portion.

On the other hand, as shown in FIG. 5A, a rotational angle of the aiming beams caused by the aperture plate 19 rotated to a preset rotational angle (FIG. 5A shows a case where the rotational angle of the aperture plate 19 was preset so as to provide the aiming beams aligned in a vertical direction) does not agree with the extending direction of the vitreous fibers, it is hard to observe both of the two aiming beams. specifically, one of the aiming beams, which falls on the vitreous fibers, is thereby reflected and may be visible to the operator, while another which falls on the outside of the vitreous fibers is invisible. When a single aiming beam is visible, the operator can not easily determine whether the alignment has been completed (namely, the two aiming beams have been overlapped each other at the same point) or only one of the two aiming beams can be viewed. In such the case, the operator rotates the knob 70 to rotate the rotation mechanism 60 so that the angular direction of the aiming beams to be irradiated agrees with the extending direction of the vitreous fibers, and he also operates the joystick 4 and others to adjust the main body 1 so as to obtain such a microscopic visual field that the portion to be cut is placed in the center and two divided aiming beams are overlapped on the portion, as shown in FIG. 5B.

When the knob 70 is used, which is provided with the click mechanism 68, the operator feels or hears a click when the rotational angle (namely, an angular direction) of the aiming beams is in the vertical direction or the horizontal direction. Thus, the operator can make a certain estimate of the current angular direction of the aiming beams even if he does not visually confirm the rotational position of the knob 70. For instance, even when the operator loses sight of the angular direction of the aiming beams during the rotation of the knob 70, due to the click mechanism 68 that provides a click at a predetermined position, he can recognize the angular direction of the aiming beams again while microscopically observing the inside of the eye E. Accordingly, the operator can promptly adjust the angular direction of the aiming beams to the extending direction of the vitreous fibers.

Successively, when the angular direction of the aiming beams irradiated from two directions is changed so that the aiming beams come to visible, as described above, the operator operates the joystick 4 and others to conduct alignment until the aiming beams are overlapped one another at the same point so as to appear in a single light spot. Fine adjustment of the alignment is conducted by rotating the knob 70 to rotate the overlapped aiming beams. If the overlapped beams are viewed to be flat, the operator adjusts such that the aiming beams come to focus. Upon completion of the alignment, the trigger switch 4a is pushed to emit the treatment beam to thereby cut the vitreous fibers of the eye E. Thus, the laser treatment for traction retinal detachment is achieved.

As described above, the case of posterior capsule incision for after cataract treatment is not much affected by the angular direction of the aiming beams. Therefore, the automatic mode is selected to automatically rotate the aiming beams. In this case, prompt confirmation of the overlapped state of two aiming beams can be conducted. In the case of requiring fine changes of the angular direction of the aiming beams, such as traction retinal detachment treatment, the manual mode is selected. In the latter case, if automatic rotation of the aiming beams is conducted, it is hard to adjust the angular direction of the aiming beams to an arbitrary angle. Also, if only one aiming beam is observed, determination of the angular direction is difficult, thus requiring much time for adjusting the angular direction of the aiming beams to the extending direction of the vitreous fibers. Consequently, since the apparatus is provided with the above mentioned mechanism for switching the rotation mode of the aiming beams between the manual mode and the automatic mode, it can efficiently conduct treatment according to disease cases.

In the manual mode, the knob 70 is rotated by the operator while the rotation of the motor 72 is made free. The operator may sense that the rotation of the knob 70 is heavy due to the engagement of the gear 75 of the knob 70 with the rotation gear 78 of the motor 72. To improve operability, a mechanism for detaching the rotation gear 78 of the motor 72 from the gear 75 of the knob 70 upon selection of the manual mode may be provided in the apparatus.

For one disease case, the manual mode and the automatic mode may be switched during operation. The manual mode is first selected to determine the angular direction of the aiming beams, and the automatic mode is next selected to finally confirm the overlapped state of the aiming beams, thereby to facilitate the observation of the aiming beams.

The present invention may be embodied in other specific forms without departing from the spirit or essential characteristics thereof. For instance, in the above embodiment according to the present invention, a single aiming light source (i.e., a laser diode) is used to form two luminous flux, but it is not limited thereto. Plural aiming light sources may be used. In addition, aperture(s), optical member(s), and others may be used to divide an aiming beam into two or more (e.g., three or four luminous flux).

As described above in detail, the laser treatment apparatus in the embodiment can facilitate adjustment and confirmation of its alignment even for a treatment area having directivity, and can conduct efficient treatment on the area, accordingly.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus for irradiating an affected area of a patient with a treatment laser beam, the apparatus including:
   a laser source which emits the treatment laser beam;
   an irradiation optical system for delivering the treatment laser beam emitted from the laser source to the affected area to irradiate it;
   an aiming light delivery optical system for forming plural aiming light beams so that an optical axis of the treatment laser beam irradiation optical system is put between the aiming light beams, and delivering the plural aiming light beams to the affected area so that the aiming light beams are focused on a position on which the treatment laser beam is to be focused;
   manual rotation means for manually rotating the aiming light beams about the irradiation optical axis;
   automatic rotation means for automatically rotating the aiming light beams about the irradiation optical axis; and
   selection means for selecting a mode to rotate the aiming light beams from a manual rotation mode conducted by the manual rotation means and an automatic rotation mode conducted by the automatic rotation means.

2. The laser treatment apparatus according to claim 1, wherein the aiming light beams are formed as at least two symmetrical luminous flux with respect to the irradiation optical axis.

3. The laser treatment apparatus according to claim 1, wherein the aiming light delivery optical system includes an aiming light source which emits aiming light and an aperture plate for dividing the aiming light emitted from the aiming light source into plural light beams.

4. The laser treatment apparatus according to claim 1, wherein the manual rotation means includes a turning knob for rotating the aiming light beams, and a rotational angle of the aiming light beams is set to be smaller than a rotational angle of the turning knob.

5. The laser treatment apparatus according to claim 1 further including rotating state recognition means for allowing an operator to recognize a rotational angle of the aiming light beams rotated by the manual rotation means.

6. The laser treatment apparatus according to claim 5, wherein the manual rotation means includes a turning knob for rotating the aiming light beams, and the rotating state recognition means includes a click mechanism which provides a click feeling to the operator through the turning knob when the rotational angle of the aiming light beams comes to a predetermined angle.

7. A laser treatment apparatus for irradiating an affected area of a patient with a treatment laser beam, the apparatus including:

a laser source which emits the treatment laser beam;

an irradiation optical system for delivering the treatment laser beam emitted from the laser source to the affected area to irradiate it;

an aiming light delivery optical system including an aiming light source which emits aiming light used for focusing the treatment laser beam to the affected area and a beam dividing member for dividing the aiming light into plural light beams so that an optical axis of the treatment laser beam irradiation optical system is put between the divided aiming light beams, and for delivering the plural aiming light beams to the affected area so that the aiming light beams are focused on a position on which the treatment laser beam is to be focused;

a rotating unit including a rotating member which holds the beam dividing member and is rotatable about the irradiation optical axis;

a knob and a first gear mechanism for manually rotating the rotating member;

a motor and a second gear mechanism for electrically rotating the rotating member;

a control unit for driving the motor; and a switch for generating a driving signal to the control unit.

8. The laser treatment apparatus according to claim 7, wherein the beam dividing member includes an aperture plate in which at least two apertures are formed symmetrically about the irradiation optical axis.

9. The laser treatment apparatus according to claim 7, wherein the rotating unit includes a click mechanism for providing a click feeling to an operator through the knob every time the rotating member is rotated at a predetermined angle with the knob.

10. The laser treatment apparatus according to claim 7, wherein the first gear mechanism includes a first gear fixed to the knob and a second gear fixed to the rotating member which engages with the first gear, and a gear ratio between the first and second gears is determined so that a rotational angle of the beam dividing member is smaller than a rotational angle of the knob.

11. The laser treatment apparatus according to claim 7, wherein the first gear mechanism includes a first gear fixed to the knob and a second gear fixed to the rotating member which engages with the first gear, and the second gear mechanism includes a third gear fixed to the knob and a fourth gear fixed to a rotating shaft of the motor which engages with the third gear.

12. The laser treatment apparatus according to claim 11, wherein the third and fourth gears detachably engages with each other.

* * * * *